United States Patent
Calderoni (10) Patent No.: US 9,502,192 B2
(45) Date of Patent: Nov. 22, 2016

(54) SURGICAL INSTRUMENTS WITH NON-CONTACT SWITCH ASSEMBLIES

(71) Applicant: Covidien LP, Mansfield, MA (US)

(72) Inventor: Anthony Calderoni, Bristol, CT (US)

(73) Assignee: Covidien LP, Mansfield, MA (US)

(*) Notice: Subject to any disclaimer, the term of this patent is extended or adjusted under 35 U.S.C. 154(b) by 89 days.

(21) Appl. No.: 14/523,399

(22) Filed: Oct. 24, 2014

(65) Prior Publication Data

US 2015/0235789 A1 Aug. 20, 2015

Related U.S. Application Data (60) Provisional application No. 61/939,987, filed on Feb. 14, 2014.

(51) Int. Cl.

| | |
|---|---|
| *G06M 7/00* | (2006.01) |
| *H01H 23/02* | (2006.01) |
| *H03K 17/969* | (2006.01) |
| *A61B 17/00* | (2006.01) |
| *A61B 17/16* | (2006.01) |

(52) U.S. Cl.
CPC ............ *H01H 23/025* (2013.01); *A61B 17/00* (2013.01); *H03K 17/969* (2013.01); *A61B 17/1622* (2013.01); *A61B 17/1626* (2013.01); *A61B 2017/0046* (2013.01); *A61B 2017/00367* (2013.01); *A61B 2017/00398* (2013.01); *A61B 2017/00734* (2013.01); *A61B 2090/0813* (2016.02); *H01H 2219/036* (2013.01); *H01H 2219/062* (2013.01); *H03K 2217/94063* (2013.01)

(58) Field of Classification Search
CPC . H01H 13/64; H01K 17/968; H01K 17/9631

USPC .......................................................... 250/221
See application file for complete search history.

(56) References Cited

U.S. PATENT DOCUMENTS

| | | | |
|---|---|---|---|
| 3,588,512 A | 6/1971 | Holtien | |
| 3,761,919 A | 9/1973 | Baumann | |
| 4,196,348 A | 4/1980 | Iwakiri et al. | |
| 4,803,362 A | 2/1989 | Butts | |
| 5,321,311 A * | 6/1994 | Umemura .............. | H01H 13/64 307/112 |

(Continued)

FOREIGN PATENT DOCUMENTS

| | | |
|---|---|---|
| CN | 101227187 A | 7/2008 |
| CN | 203014768 U | 6/2013 |

(Continued)

OTHER PUBLICATIONS

European Search Report dated Oct. 27, 2015, issued in European Application No. 14199771.

*Primary Examiner* — Thanh Luu (57) ABSTRACT

A non-contact button assembly for a powered surgical instrument includes a light emitter, a rocker switch, and a button shaft. The rocker switch defines a through passage about a longitudinal axis of the button assembly. The button shaft is disposed within the through passage. The button shaft includes a proximal portion, a distal portion, and a flange positioned therebetween. The button shaft has a deactivated position such that the button shaft is configured to prevent light from the light emitter from illuminating a light detector and the button shaft has an activated position such that the button shaft is configured to permit light emitted from the light emitter to illuminate the light detector.

17 Claims, 6 Drawing Sheets

(56) References Cited

U.S. PATENT DOCUMENTS

| | | | |
|---|---|---|---|
| 2010/0171026 A1* | 7/2010 | Saitou | H03K 17/968 250/221 |
| 2012/0089131 A1* | 4/2012 | Zemlok | A61B 17/07207 606/1 |
| 2012/0253329 A1 | 10/2012 | Zemlok et al. | |
| 2012/0296159 A1 | 11/2012 | Kanazawa et al. | |

FOREIGN PATENT DOCUMENTS

| | | |
|---|---|---|
| GB | 1540428 A | 2/1979 |
| KR | 20020020332 A | 3/2002 |
| KR | 20070000199 U | 2/2007 |
| WO | 2008147415 A1 | 12/2008 |

\* cited by examiner

SURGICAL INSTRUMENTS WITH NON-CONTACT SWITCH ASSEMBLIES

CROSS-REFERENCE TO RELATED APPLICATIONS

This application claims the benefit of and priority to U.S. Provisional Patent Application No. 61/939,987, filed Feb. 14, 2014, the entire disclosure of which is incorporated by reference herein.

BACKGROUND

1. Technical Field

The present disclosure relates to surgical instruments and, more specifically, to powered surgical instruments including non-contact switch block assemblies.

2. Discussion of Related Art

Powered surgical instruments generally have a handle portion including a plurality of control buttons and switches to control electrical components within the handle portion and a working portion extending from the handle portion that contacts a patient. After each use, the powered surgical instrument is disposed of, reused, or partially disposed of and partially reused. Any part of a powered surgical instrument that is reused must be sterilized to neutralize potentially infectious agents before being reused.

The autoclave process has been used for many years to sterilized reusable surgical instruments. However, the steam and the high-pressure used in the autoclave process can damage electrical components within the housing.

The plurality of control buttons and switches must be able to withstand repeated exposure to the autoclave process. A common solution is to seal the plurality of control buttons and switches or cover the plurality of control buttons and switches with membranes. However, cyclic pressurizing and depressurizing of the plurality of control buttons and switches fatigue the seals or membranes. As a consequence of this fatigue, steam can enter the plurality of control buttons and switches causing the powered surgical instrument to fail.

Accordingly, a continuing need exists for control buttons and switches that can withstand cyclical pressurizing and depressurizing.

SUMMARY

In an aspect of the present disclosure, a non-contact button assembly for a powered surgical instrument includes a light emitter configured to emit light, a light detector, a rocker switch, a rocker housing, a button retainer, and a button shaft. The rocker switch has a proximal end portion and defines a through passage about a longitudinal axis thereof through the proximal end portion. The rocker housing is positioned about the proximal end portion of the rocker switch to retain the rocker switch within the rocker housing. The button shaft is disposed within the through passage of the rocker switch and includes a proximal portion, a distal portion, and a flange positioned between the proximal and distal portions. The button shaft has a deactivated position such that the button shaft is configured to prevent light from the light emitter from illuminating the light detector and the button shaft has an activated position such that the button shaft is configured to permit light emitted from the light emitter to illuminate the light detector.

In embodiments, the button shaft defines a through slot orthogonal to a longitudinal axis thereof. In such embodiments, the through slot may be aligned with the light emitter in the activated position and offset from the light emitter in the deactivated position. The through slot may be positioned distal to the flange.

In some embodiments, the proximal portion of the button shaft defines an opening and the light emitter is positioned within the opening. The light emitter may be configured to emit light from the opening towards the light detector. A cover may be coupled to the proximal portion of the button shaft adjacent the opening. In a closed configuration of the cover, the cover is configured to prevent light from the light emitter from illuminating a light detector and in an open configuration of the cover, the cover is configured to permit light to illuminate the light detector. The cover may include a tap extending beyond an outer surface of the proximal portion of the button shaft that is configured to engage the rocker housing to transition the cover to the open position when the button shaft is in the activated position.

In embodiments, the button assembly further includes a control button secured to the distal portion of the button shaft. The control button may be threadably secured to the distal portion of the button shaft.

In some embodiments, the light emitter is a light pipe configured to transmit light from the light source. A light pipe may be configured to transmit light from the light emitter to illuminate a light detector.

In embodiments, the button assembly further includes a rocker disc and a second light emitter. The rocker disc defines an activation slot and cooperates with the rotation of the rocker switch about the longitudinal axis. In a deactivated position of the rocker switch, the second light emitter is offset from the activation slot and the rocker disc prevents light emitted from the second light emitter from illuminating a light detector. In an activated position of the rocker disc, the second light emitter is aligned with the activation slot to illuminate a light detector through the activation slot.

In preferred embodiments, the light emitter is configured to encode light emitted therefrom and the detector is configured to selectively respond to encoded signals.

In aspects of the present disclosure, a surgical handle includes a handle housing, a control assembly, and a switch block assembly. The control assembly includes a first light detector sealed within the handle housing and the switch block assembly includes a switch block fixed to the handle housing. The switch block includes a first non-contact button assembly having a first light emitter configured to emit light. The first non-contact button assembly further includes a rocker switch, a rocker housing, a button retainer, and a button shaft. The rocker switch includes a proximal end portion and defines a through passage through the proximal end portion about a longitudinal axis thereof. The rocker housing is positioned about the proximal end portion of the rocker switch and the button retainer is secured about the proximal end portion of the rocker switch to retain the rocker switch within the rocker housing. The button shaft is disposed within the through passage of the rocker switch. The button shaft has a proximal portion, a distal portion, and a flange positioned therebetween. The button shaft has a deactivated position such that the button shaft is configured to prevent light from the light emitter from illuminating the first light detector and the button shaft has an activated position such that the button shaft is configured to permit light emitted from the light emitter to illuminate the first light detector.

In embodiments, the handle includes a drive component operatively associated with the first light detector such that the control assembly is configured to activate the drive component when the first light detector is illuminated by light emitted from the first light emitter.

In some embodiments, the handle housing is sealed from the switch block and the control assembly includes a first light source positioned within the handle housing and the first light emitter includes a fiber optic light pipe configured to receive light from the first light source.

In embodiments, the control assembly includes a second light detector and the switch block includes a second non-contact button assembly. The second non-contact button assembly includes a rocker switch, a rocker housing, a button retainer, and a button shaft. The rocker switch includes a proximal end portion positioned and defines a through passage through the proximal end portion about a longitudinal axis thereof. The rocker housing is positioned about the proximal end portion of the rocker switch and the button retainer is secured about the proximal end portion of the rocker switch to retain the rocker switch within the rocker housing. The button shaft is disposed within the through passage of the rocker switch. The button shaft has a proximal portion, a distal portion, and a flange positioned therebetween. The button shaft has a deactivated position such that the button shaft is configured to prevent light from the light emitter from illuminating the second light detector and the button shaft has an activated position such that the button shaft is configured to permit light emitted from the light emitter to illuminate the second light detector. The first light detector may be configured to activate a drive component operatively associated with the first light detector when the first light detector is illuminated with light emitted from the first light emitter. The first light detector may be configured to not sense light emitted from the second light emitter such that the first light detector does not activate the drive component when illuminated by light from the second light emitter. In some embodiments, the control assembly includes third and fourth light detectors such that the rocker switch of the first non-contact control button assembly is operatively associated with a third light emitter and the rocker switch of the second non-contact control button assembly is operatively associated with a fourth light emitter.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is furthest from the clinician.

Figure 1:
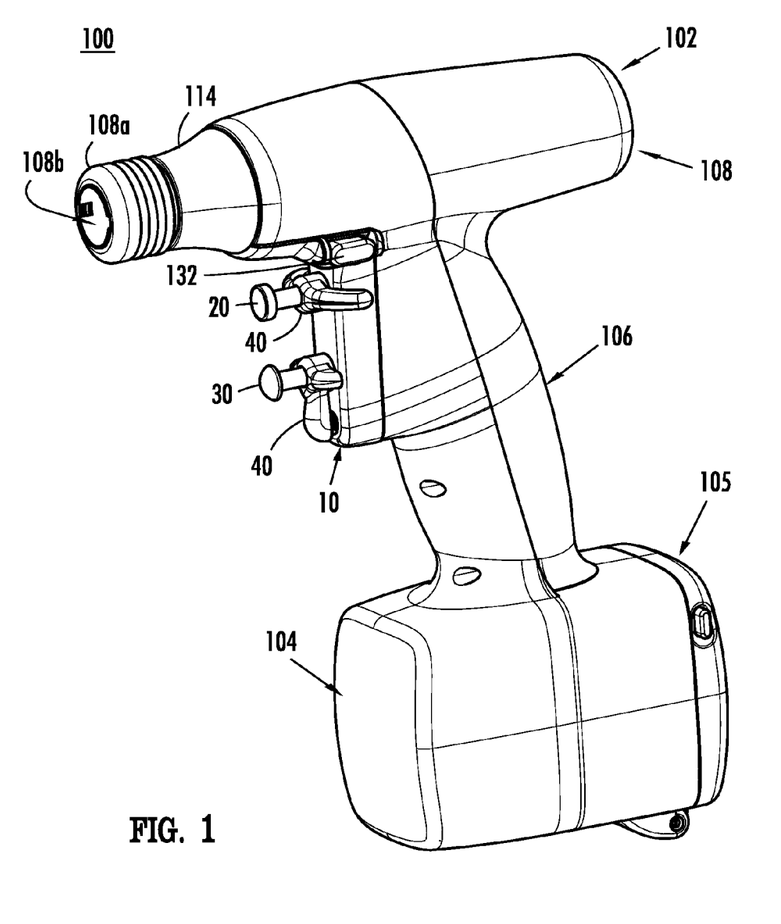
FIG. 1 is a perspective view of an exemplary powered surgical handle in accordance with the present disclosure including a non-contact switch block assembly.

Referring to FIG. 1, an exemplary embodiment of a surgical handle 100 provided in accordance with the present disclosure. The surgical handle 100 is a powered hand held electromechanical instrument configured for selective attachment thereto of a plurality of different end effectors that are each configured for actuation and manipulation by the powered hand held electromechanical surgical instrument. An exemplary example of such a powered hand held electromechanical surgical instrument is disclosed in commonly owned and co-pending U.S. patent application Ser. No. 13/331,047, filed Dec. 20, 2011 and published as U.S. Patent Pub. No. 2012/0089131 on Apr. 12, 2012, and Ser. No. 13/484,975, filed May 31, 2012 and published as U.S. Patent Pub. No. 2012/0253329 on Oct. 4, 2012, the contents of each are hereby incorporated by reference in its entirety.

Figure 2:
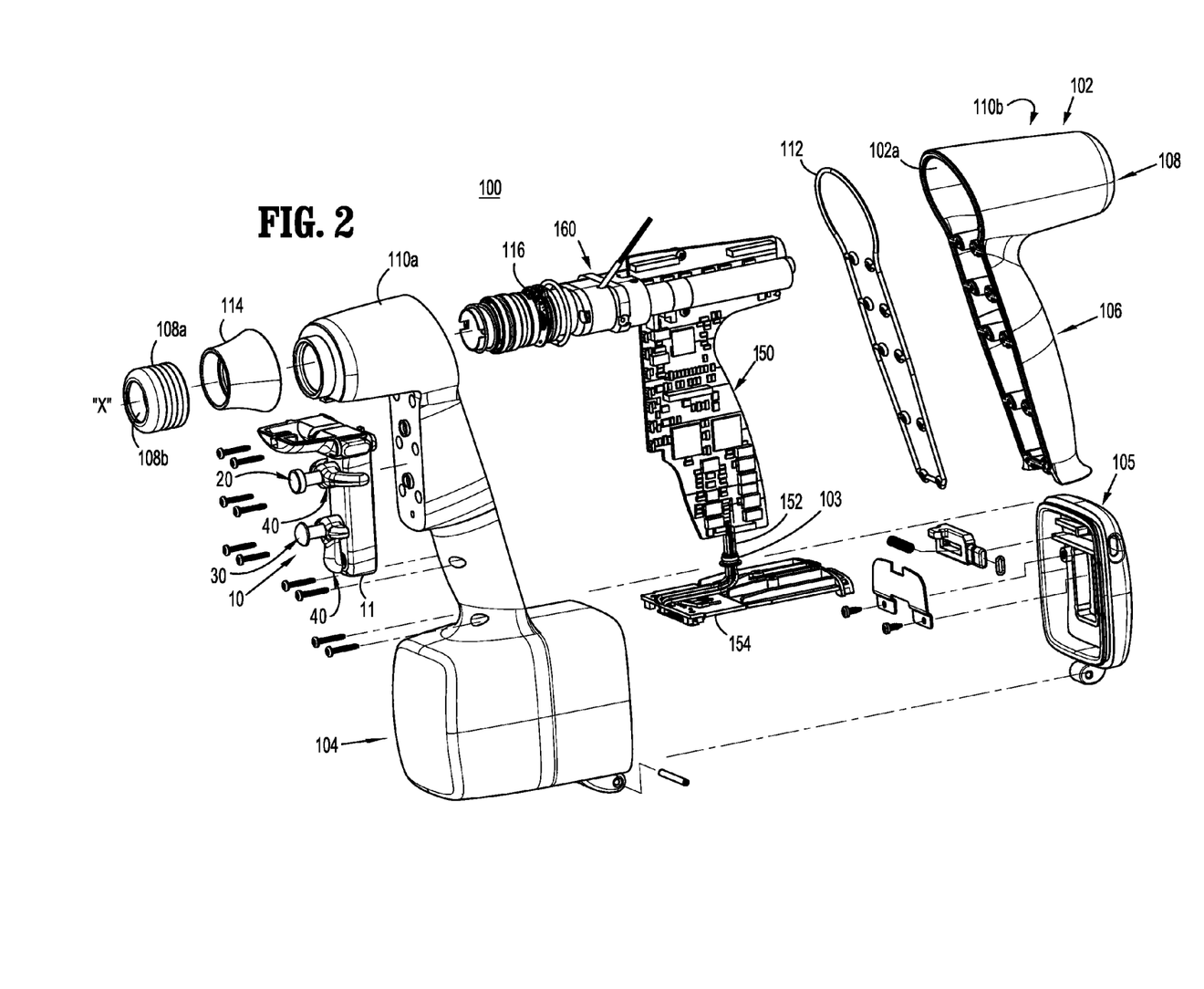
FIG. 2 is an exploded view of the powered surgical handle of FIG. 1 illustrating the components thereof.

As illustrated in FIGS. 1 and 2, the surgical handle 100 includes a handle housing 102 having a lower housing portion 104, an intermediate housing portion 106 extending from and/or supported on the lower housing portion 104, and an upper housing portion 108 extending from and/or supported on the intermediate housing portion 106. The intermediate and upper housing portions 106, 108 are separated into a distal half-section 110a that is integrally formed with and extending from the lower portion 104, and a proximal half-section 110b connectable to the distal half-section 110a by a plurality of fasteners. When joined, the distal and proximal half-sections 110a, 110b define a handle housing 102 having a cavity 102a therein in which a circuit board 150 and a drive mechanism 160 is situated.

The handle housing 102 includes a gasket 112 extending completely around a rim of the distal half-section 110a and/or proximal half-section 110b and being interposed between the distal and proximal half-sections 110a, 110b. The gasket 112 seals the perimeter of the distal and proximal half-sections 110a, 110b. The gasket 112 functions to establish an airtight seal between the distal and proximal half-sections 110a, 110b such that the circuit board 150 and the drive mechanism 160 are protected from sterilization and/or cleaning procedures.

The intermediate housing portion 106 of the handle housing 102 provides a housing in which the circuit board 150 is situated. The circuit board 150 is configured to control the various operations of the surgical handle 100, as detailed below.

As shown, the lower housing portion 104 of the handle housing 102 provides a housing in which a rechargeable battery (not shown) is removably situated. The battery is configured to supply power to any of the electrical components of the surgical handle 100. The lower housing portion 104 defines a cavity (not shown) into which the battery is inserted. The lower housing portion 104 includes a door 105 pivotally connected thereto for closing the cavity of the lower housing portion 104 and retaining the battery therein.

Figure 3:
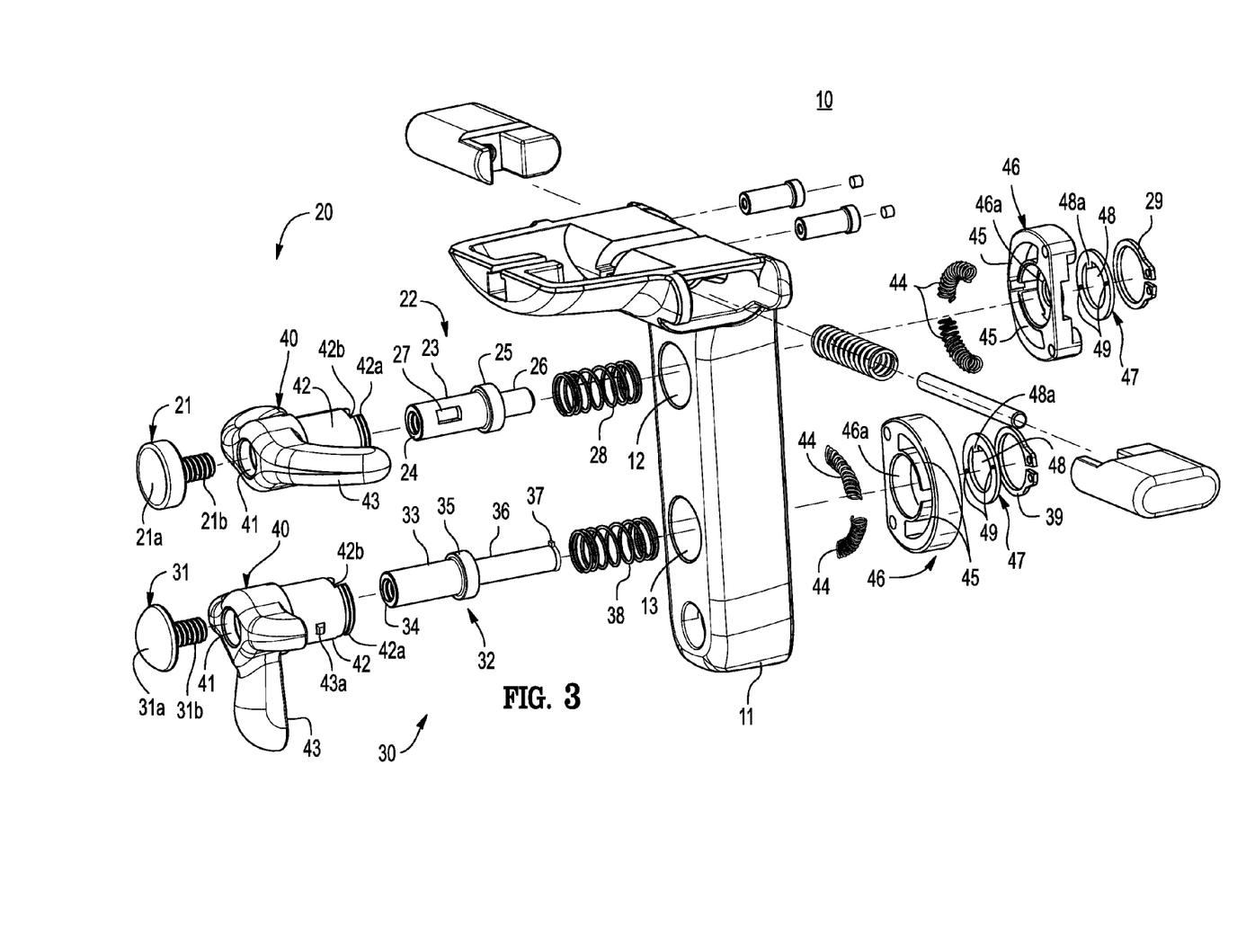
FIG. 3 is an exploded view of the switch block assembly of FIG. 2 illustrating the components thereof.

With reference to FIGS. 2 and 3, the handle housing 102 supports a switch block assembly 10 on a distal surface or side of the intermediate housing portion 106. The switch block assembly 10 includes a switch block 11, a pair of button receiving holes 12, 13, and a pair of finger-actuated control button assemblies 20, 30 received within the button receiving holes 12, 13, respectively. The switch block 11 may form an airtight seal between itself and the distal surface of the intermediate housing portion 106. The switch block 11 supports the pair of control button assemblies 20, 30. The button receiving holes 12, 13 may be blind, stepped, or through holes. Each of the control button assemblies 20, 30 include a rocker switch 40. Each of the control button assemblies 20, 30 functions in a non-contact manner to control various operations of the surgical handle 100, as detailed below. It will be understood that the switch block 11 forms a seal with the intermediate housing portion 106 and that the control button assemblies 20, 30 operate in a non-contact manner to maintain the seal of the cavity 102a during surgical, sterilization, and/or cleaning procedures.

Figure 4:
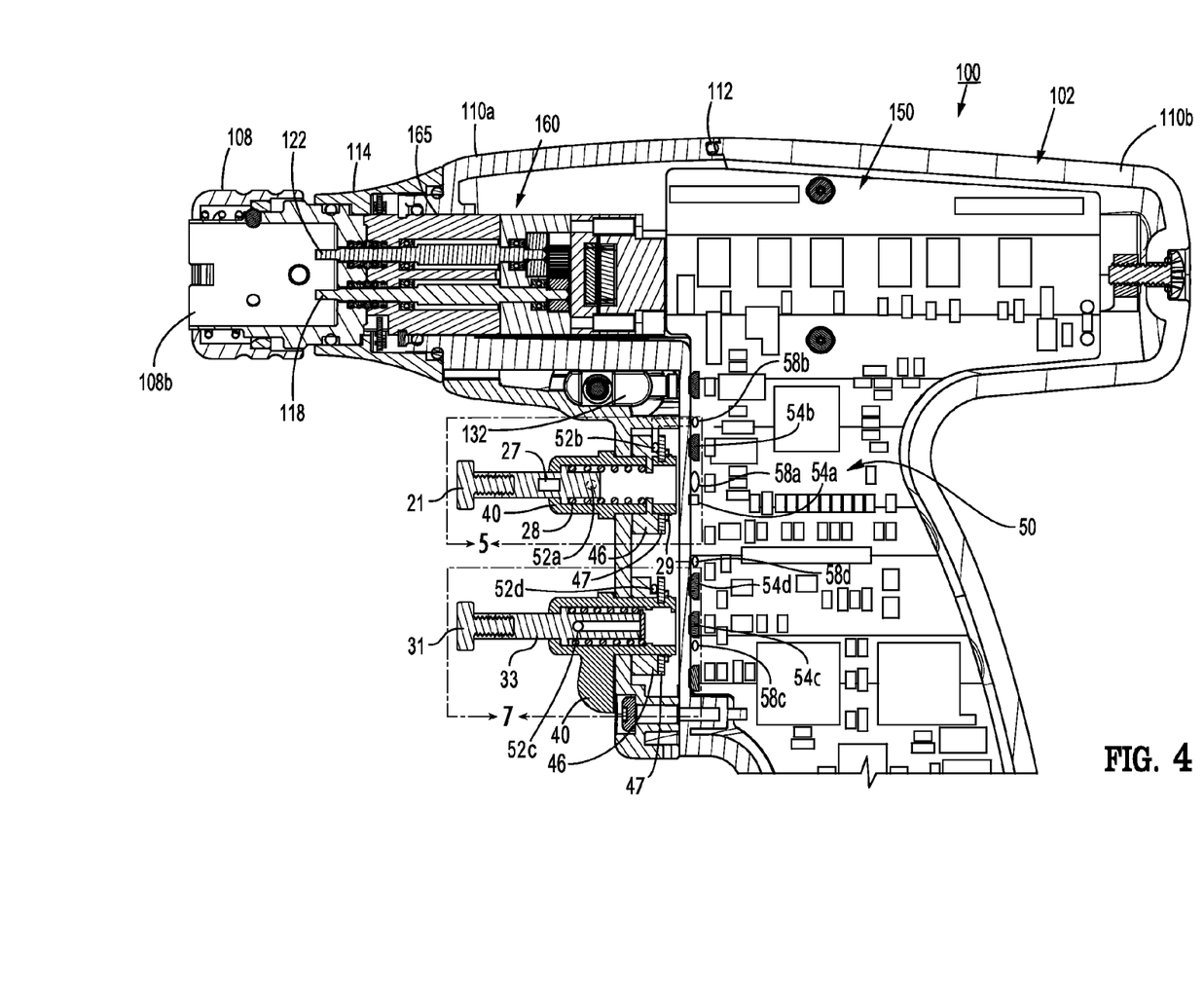
FIG. 4 is a side cross-sectional view of the surgical handle of FIG. 1 taken along the longitudinal axis thereof.

With reference to FIGS. 2 and 4, the handle 100 includes a control assembly 50 disposed on the circuit board 150 having light emitters 52a-d and sensors 54a-d. Each of the sensors 54a-d operatively associate a respective one of the control button assemblies 20, 30 or rocker switches 40 with one or more of the drive components of the handle 100. When the respective one of the control button assemblies 20, 30 or rocker switches 40 is in a deactivated position, light from the respective light emitter 52a-d is prevented from contacting the respective one of the sensors 54a-d. When the respective one of the control button assemblies 20, 30 or rocker switches 40 is in an activated position, light from the respective light emitter 52a-d is received by the one of the respective sensors 54a-d as detailed below.

The light emitted by each light emitter 52a-d may be coded and/or encrypted to only one of the respective sensors 54a-d such that when light from one light emitter 52a-d illuminates a sensor 54a-d not associated with the respective one of the light emitters 52a-d, the sensor 54a-d does not activate a drive component(s) associated with the respective sensor 54a-d as detailed below. In embodiments, each light emitter 52a-d emits light at a specific wavelength or wavelengths within the UV spectrum, the visible spectrum, or the IR spectrum to encode the light to one or more respective sensors 54a-d. In some embodiments, each light emitter 52a-d emits light in a specific pattern to encode the light to a respective one of the sensors 54a-d. It is contemplated that one light emitter 52a-d may emit light configured to be received by more than one sensor 54a-d or that one sensor 54a-d may be configured to activate a drive component in response to light emitted from more than one of the light emitters 52a-d.

Each of the control button assemblies 20, 30 and rocker switches 40 are operatively associated with one or more drive components of the handle 100 (e.g., drive shafts 118, 122) in a non-contact manner. Each of the drive components of the handle 100 controls a function of an end effector (not shown) engaged directly with the handle 100, or indirectly with the handle via an adapter (not shown). The functions of the end effector engaged with the handle may include but are not limited to clamping tissue, articulating the end effector, rotating the end effector, firing staples, firing a clip, forming a suture, cutting tissue, etc. In the deactivated position, the drive component operatively associated with the control button assemblies 20, 30 and rocker switches 40 is not actively driven by the handle 100. It is contemplated that when a drive component is not actively driven by the handle 100, that external forces on the end effector may result in movement of the drive component (e.g., an end effector may articulate when contacting tissue which may result in rotation of the drive component associated with articulation of the end effector). It is further contemplated that when a drive component is not actively driven, that the drive component is locked preventing movement of a component of the end effector (e.g., when an end effector contacts tissue the end effector resists movement).

Figure 5:
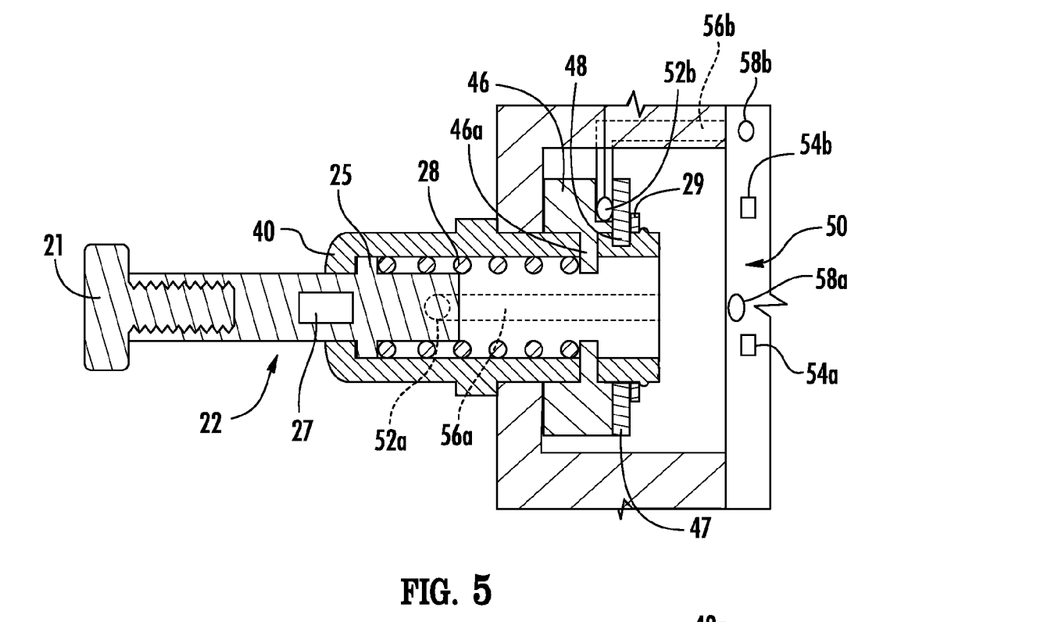
FIG. 5 is an enlarged view of the detail area 5 of FIG. 4 showing a control switch assembly and a rocker switch in a deactivated position.

Referring now to FIGS. 3-5, the control button assembly 20 includes a control button 21, a rocker switch 40, a button shaft 22, a button-biasing member 28, a pair of rocker-biasing members 44, a rocker housing 46, a rocker disc 47, and a button retainer 29. The control button 21 includes an engagement surface 21a facing away from the switch block 11 for selective activation of control button 21 and a threaded shaft 21a extending towards the switch block 11. The engagement surface 21a of control button 21 may be convex, concave, or textured to provide tactile feedback to the clinician as to which button is engaged. The button shaft 22 includes a distal portion 23, a proximal portion 26, and a flange 25 positioned between the distal and proximal portions 23, 26 of the button shaft 22. The distal portion 23 defines a threaded hole 24 that cooperates with the threaded shaft 21b of the control button 21 to secure the control button 21 to the distal portion 23 of the button shaft 22. The threaded hole 24 may be a blind hole or may extend through the button shaft 22. The flange 25 extends beyond the outer surface of the distal and proximal portions 23, 26 to prevent the button shaft 22 from passing through the rocker switch 40. The through slot 27 is defined through the proximal portion 26 of the button shaft 22, orthogonal to the longitudinal axis of the button shaft 22.

The rocker switch 40 defines a stepped through passage 41 and includes a proximal end portion 42 and an actuation arm 43. The distal portion 23 of the button shaft 22 is received within the stepped through passage 41 of the rocker switch 40 such that the button shaft 22 may longitudinally slide relative to the rocker switch 40 and the rocker switch 40 may rotate about the button shaft 22. The proximal end portion 42 passes through the rocker housing 46 and the rocker disc 47. The proximal end portion 42 defines a keyway 42a parallel to the longitudinal axis thereof. The rocker disc 47 is disposed over the proximal end portion 42 of the rocker switch 40 between the rocker housing 46 and the button retainer 29. The rocker disc 47 defines a central opening 48 that includes a key 48a to radially align the rocker disc 47 with the rocker switch 40. The rocker disc 47 further defines activation slots 49 through the surfaces of the rocker disc 47 as detailed below. The proximal end portion 42 of rocker switch 40 further defines a retaining groove 42b adjacent a proximal end thereof. The button retainer 29 is received within the retaining groove 42b to secure the button assembly 20 together.

The button-biasing member 28 engages the flange 25 to urge the button shaft 22 distally towards a deactivated position, i.e., away from or out of switch block 11. The button-biasing member 28 is disposed over the proximal portion 26 of the button shaft 22 between the flange 25 of the button shaft 22 and the retainer housing 46. The retainer housing 46 includes a step 46a to prevent the button-biasing member 28 from passing through the retainer housing 46.

The pair of rocker-biasing members 44 urge the rocker switch 40 to a neutral or deactivated position. The pair of rocker-biasing members 44 are disposed within an arcuate slot 45 of the rocker housing 46. The rocker switch 40 includes a biasing-protrusion 43*a* positioned between the pair of rocker-biasing members 44 within the arcuate slot 45. Each of the pair of rocker-biasing members 44 engages the biasing-protrusion 43 such that when no external force is applied to the rocker switch 40 (e.g., a finger engaging the arm 43) the rocker-biasing members 44 engage the biasing-protrusion 43 with equal force to urge the rocker switch 40 to the deactivated position.

Figure 6:
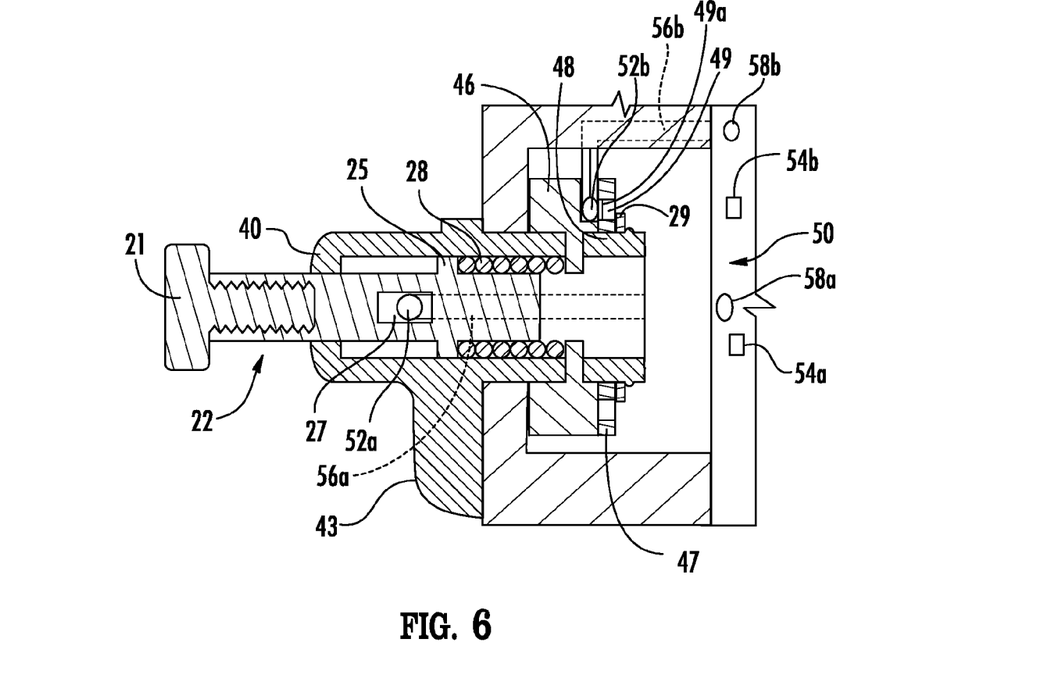
FIG. 6 is a side view of the control switch assembly and the rocker switch of FIG. 5 in an activated position.

With reference to FIGS. 5 and 6, the control button 21 has a deactivated position (FIG. 5) and an activated position (FIG. 6). The light emitter 52*a* is positioned along the distal portion 23 of the button shaft 22 such that light is emitted from the light emitter 52*a* towards the button shaft 22. When the control button 21 is in the deactivated position (FIG. 4), the slot 27 is offset from the light emitter 52*a* such that light emitted from light emitter 52*a* does not pass through the slot 27 to illuminate the sensor 54*a*. When the control button 21 is depressed against the button-biasing member 28 to the activated position (FIG. 5), the slot 27 is aligned with the light emitter 52*a* such that light emitted from the light emitter 52*a* passes through the slot 27 to illuminate the sensor 54*a*. As detailed above, when the light emitter 52*a* illuminates the sensor 54*a*, the sensor 54*a* sends a signal to activate one or more drive component(s) associated with sensor 54*a*. It is also contemplated that in the deactivated position the light emitter 52*a* may illuminate the sensor 54*a* and in the activated position the light emitter 52*a* is prevented from illuminating the sensor 54*a* (e.g., the slot 27 is aligned with the light emitter 52*a* in the deactivated position and offset from the light emitter 52*a* in the activated position).

With continued reference to FIGS. 5 and 6, the rocker switch 40 has a deactivated position (FIG. 5) and an activated position (FIG. 6). The light emitter 54*b* is positioned about the rocker disc 47 such that light emitted from the light emitter 54*b* is directed towards the rocker disc 47 and the sensor 54*b*. When the rocker switch 40 is in the deactivated position (FIG. 5), the activation slots 49 are offset from the light emitter 54*b* with the rocker disc 47 preventing the light emitter 54*b* from illuminating the sensor 54*b*. When the rocker switch 40 is rotated about the button shaft 22 to the activated position (FIG. 5), one of the activation slots 49 is aligned with the light emitter 52*b* to permit light from the light emitter 52*b* to pass through one of the activation slots 49 to illuminate the sensor 54*b*. One of the activation slots 49 may include a film or filter 49*a* to alter the light emitted from source 52*b* to encrypt the light illuminating sensor 54*b* to indicate which one of the activation slots 49*b* is aligned with the light emitter 52*b*. It is contemplated, that the filter 49*a* may allow the sensor 54*b* to activate the drive component in a particular direction (e.g., if the drive component is for articulation, the filter 49*a* may alter the light emitted form the light emitter 52*b* to indicate that the rocker switch 40 was rotated clockwise to articulate an end effector (not shown) to the right and unaltered light from the light emitter 52*b* indicates that the rocker switch 40 was rotated counterclockwise to articulate the end effector to the left). It is contemplated that slot 27 may include a similar film or filter to alter or encrypt light emitted from a respective one of the light emitters 52*a-d*.

It is also contemplated that activation slots 49 may be disposed about the perimeter of the rocker disc 47 such that as the rocker disc 47 is rotated from the deactivated position towards the activated position, the amount of light illuminating the sensor 54*b* increases as the rocker disc 47 approaches the activated position. The sensor 54*b* is configured to detect the increased amount of light (e.g., intensity) to increase the energy sent to a drive component operatively associated with the sensor 54*b* (e.g., increase a rotational speed or torque supplied to the drive component). It is also contemplated that film 49*a* may vary the light passing through the activation slot 49 as the rocker disc 47 is rotated to change a property of the light (e.g., the wave length, the intensity, etc.) to increase or decrease the energy sent to a drive component operatively associated with the sensor 54*b*.

Figure 7:
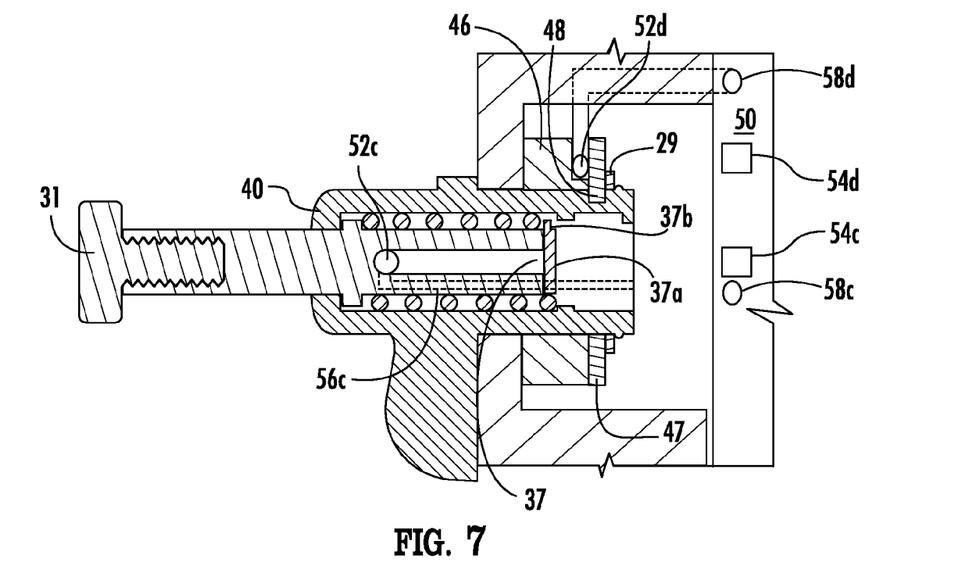
FIG. 7 is an enlarged view of the detail area 7 of FIG. 4 showing a control switch assembly and a rocker switch in a deactivated position.

Referring now to FIGS. 3, 4, and 7, the button assembly 30 includes a control button 31, a rocker switch 40, a button shaft 32, a button-biasing member 38, a pair of rocker-biasing members 44, a rocker housing 46, a rocker disc 47, and a button retainer 39. The control button 31, switch biasing-member 38, and button retainer 39 of the switch assembly 30 are substantially similar to the control button 21, switch biasing-member 28, and button retainer 29 of the switch assembly 20 detailed above, as such only the differences and the relation with other components of the button assembly 30 will be detailed herein.

The button shaft 32 includes a distal portion 33, a proximal portion 36, and a flange 35 positioned between the distal and proximal portions 33, 36. The distal portion 33 defines a threaded hole 34 that cooperates with a threaded shaft 31*b* of the control button 31 to secure the control button 31 to the distal portion 33 of the button shaft 32. The threaded hole 34 may be a blind hole or may extend through the button shaft 32. The flange 35 extends beyond the outer surface of the distal and proximal portions 33, 36 to prevent the button shaft 32 from passing through the rocker switch 40.

The proximal end of the proximal portion 36 defines an opening 37. The opening 37 may form a through hole with threaded hole 34 that passes through the button shaft 32. A light emitter 52*c* is positioned within the opening 37. The button assembly 30 further includes a cover 37*a* adjacent opening 37.

Figure 8:
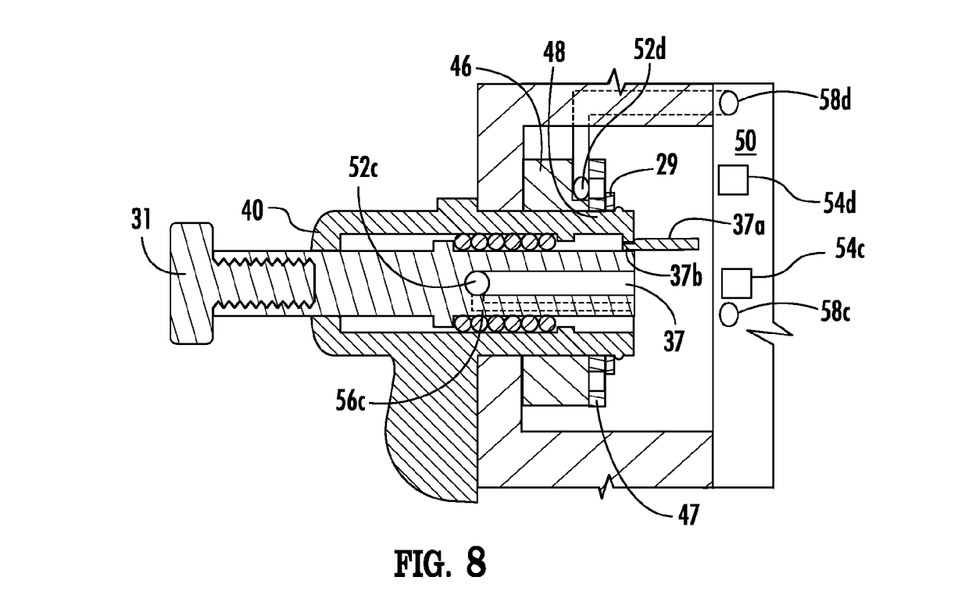
FIG. 8 is a side view of the control switch assembly and the rocker switch of FIG. 7 in an activated position.

With reference to FIGS. 7 and 8, the cover 37 has a closed condition (FIG. 7) and an open condition (FIG. 8) corresponding to the deactivated position and the activated position, respectively. In the closed condition, the cover 37 prevents light from the light emitter 52*c* from exiting the opening 37 and in the open condition, light from light emitter 52*c* exits the opening 37 to illuminate a sensor 54*c*. The cover 37*a* is coupled about the proximal end of the proximal portion 36 and includes a tab 37*b* extending radially therefrom. As the button 31 is depressed, the tab 37*b* engages the rocker housing 46 to transition the cover 37*a* to the open condition. In embodiments, the cover 37*a* includes two halves overlapping along a centerline of the cover 37*a* with each half of the cover 37*a* including a tab 37*b*.

The light emitter 52*c* is positioned within the opening 37 as detailed above. The sensor 54*c* is aligned with the light emitter 52*c* such that light emitted from the opening 37 will illuminate the sensor 54*c*. As shown, sensor 54*c* is aligned with the longitudinal axis of the button shaft 33; however, it is contemplated that the sensor 54*c* may be offset from the longitudinal axis of the button shaft 33 and a surface of the cover 37*a* may deflect light towards the sensor 54*c*. In the deactivated position (FIG. 7), the cover 37*a* is in the closed condition preventing light from the light emitter 52*c* from illuminating the sensor 52*c*. When the control button 31 is depressed against the button-biasing member 38 to the activated position (FIG. 8), the tab 37*b* of the cover 37*a* engages a portion of the retainer housing 46 to transition cover 37*a* to the open condition permitting light emitting from the light emitter 52*c* to illuminate the sensor 52*c*.

With reference to FIGS. 5-8, each light emitter 52a-d may be operatively associated with a light source 58a-d by a light pipe 56a-d. For example, with particular reference to FIG. 5, the light emitter 52b may be operatively associated with a light source 58b by a light pipe 56b passing through a portion of the switch block 11. The light pipe 56b may be a fiber optic cable with one end positioned adjacent the light source 58b and the other end positioned adjacent the light emitter 52b. It is also contemplated that the light emitter 52b is integrally formed with one end of the light pipe 56b. It is also contemplated that a light pipe (e.g., light pipe 56a) may be configured to transmit received from a light emitter to a light detector (e.g., light detector 54a).

It will be understood that the operation of the rocker switch 40 associated with button assembly 30 is similar to the operation of the rocker switch 40 associated with button assembly 20; as such the operation of the rocker switch 40 associated with button assembly 20 will not be detailed below for reasons of brevity.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A non-contact button assembly for a powered surgical instrument, the button assembly comprising:
    a light emitter configured to emit light;
    a rocker switch having a proximal end portion, the rocker switch defining a through passage about a longitudinal axis thereof through the proximal end portion;
    a rocker housing positioned about the proximal end portion of the rocker switch;
    a button retainer secured about the proximal end portion of the rocker switch to retain the rocker switch within the rocker housing; and
    a button shaft disposed within the through passage of the rocker switch, the button shaft having a proximal portion, a distal portion, and a flange positioned between the proximal and distal portions, the proximal portion defining an opening, the light emitter positioned within the opening and configured to emit light from the opening, the button shaft has a deactivated position, wherein the button shaft is configured to prevent light from the light emitter from illuminating a light detector, and the button shaft has an activated position, wherein the button shaft is configured to permit light emitted from the light emitter to illuminate the light detector, the button shaft including:
        a cover coupled to the proximal portion thereof and adjacent the opening thereof, the cover having a closed configuration, wherein the cover is configured to prevent light from the light emitter from illuminating a light detector, and an open configuration, wherein the cover is configured to permit light to illuminate the light detector.

2. The button assembly of claim 1, wherein the button shaft defines a through slot orthogonal to a longitudinal axis thereof, wherein in the activated position the through slot is aligned with the light emitter and in the deactivated position the through slot is offset from the light emitter.

3. The button assembly of claim 2, wherein the through slot is distal to the flange.

4. The button assembly of claim 1, wherein the cover includes a tab extending beyond an outer surface of the proximal portion, wherein when the button shaft is in the activated position the tab engages the rocker housing to transition the cover to the open position.

5. The button assembly of claim 1 further including a control button secured to the distal portion of the button shaft.

6. The button assembly of claim 5, wherein the control button is threadably secured to the distal portion of the button shaft.

7. The button assembly of claim 1, wherein the light emitter is a light pipe configured to transmit light from a light source.

8. The button assembly of claim 1, wherein a light pipe is configured to transmit light from the light emitter to illuminate a light detector.

9. The button assembly of claim 1, wherein the light emitter is configured to encode light emitted therefrom.

10. The button assembly of claim 1, wherein the button shaft is configured to be depressed from the deactivated position to the activated position.

11. A non-contact button assembly for a powered surgical instrument, the button assembly comprising:
    a light emitter configured to emit light;
    a rocker switch having a proximal end portion, the rocker switch defining a through passage about a longitudinal axis thereof through the proximal end portion;
    a rocker housing positioned about the proximal end portion of the rocker switch;
    a button retainer secured about the proximal end portion of the rocker switch to retain the rocker switch within the rocker housing;
    a button shaft disposed within the through passage of the rocker switch, the button shaft having a proximal portion, a distal portion, and a flange positioned between the proximal and distal portions, the button shaft has:
        a deactivated position, wherein the button shaft is configured to prevent light from the light emitter from illuminating a light detector; and
        an activated position, wherein the button shaft is configured to permit light emitted from the light emitter to illuminate the light detector;
    a rocker disc defining an activation slot, the rocker disc cooperating with rotation of the rocker switch about the longitudinal axis; and
    a second light emitter offset from the activation slot, the rocker switch having a deactivated position in which the rocker disc is configured to prevent light emitted from the second light emitter from illuminating a light detector, and an activated position in which the second light emitter is aligned with the activation slot and the activation slot of the rocker disc is configured to permit light emitted from the second light emitter to illuminate a light detector.

12. A surgical handle comprising:
    a handle housing;
    a control assembly including first and second light detectors sealed within the handle housing; and
    a switch block assembly including a switch block fixed to the handle housing, the switch block having first and second non-contact control button assemblies, the first non-contact control button assembly having:

a first light emitter configured to emit light;

a rocker switch having a proximal end portion, the rocker switch defining a through passage about a longitudinal axis thereof;

a rocker housing positioned about the proximal end portion of the rocker switch;

a button retainer secured about the proximal end portion of the rocker switch to retain the rocker switch within the rocker housing; and a button shaft disposed within the through passage of the rocker switch, the button shaft having a proximal portion, a distal portion, and a flange positioned between the proximal and distal portions, the button shaft has a deactivated position, wherein the button shaft is configured to prevent light from the first light emitter from illuminating the first light detector, and the button shaft has an activated position, wherein the button shaft is configured to permit light emitted from the first light emitter to illuminate the first light detector; and the second non-contact control button assembly having:

a second light emitter configured to emit light;

a rocker switch having a proximal end portion, the rocker switch defining a through passage about a longitudinal axis thereof;

a rocker housing positioned about the proximal end portion of the rocker switch;

a button retainer secured about the proximal end portion of the rocker switch to retain the rocker switch within the rocker housing; and a button shaft disposed within the through passage of the rocker switch, the button shaft having a proximal portion, a distal portion, and a flange positioned between the proximal and distal portions, the button shaft has a deactivated position, wherein the button shaft is configured to prevent light from the second light emitter from illuminating the second light detector, and the button shaft has an activated position, wherein the button shaft is configured to permit light emitted from the second light emitter to illuminate the second light detector.

13. The handle of claim 12 further including a drive component operatively associated with the first light detector, the control assembly configured to activate the drive component when the first light detector is illuminated by light emitted from the first light emitter.

14. The handle of claim 12, wherein the handle housing is sealed from the switch block, the control assembly includes a first light source positioned within the handle housing, and the first light emitter includes a fiber optic light pipe configured to receive light from the first light source.

15. The handle of claim 12, wherein the first light detector is configured to activate a drive component operatively associated with the first light detector when the first light detector is illuminated with light emitted from the first light emitter.

16. The handle of claim 15, wherein the first light detector is configured to not sense light emitted from the second light emitter.

17. The handle of claim 15, wherein the control assembly includes third and fourth light detectors and the rocker switch of the first non-contact control button assembly is operatively associated with a third light emitter and the rocker switch of the second non-contact control button.

\* \* \* \* \*